(12) United States Patent
Clark et al.

(10) Patent No.: US 7,745,676 B2
(45) Date of Patent: Jun. 29, 2010

(54) ALKYLAROMATICS PRODUCTION

(75) Inventors: Michael C. Clark, Chantilly, VA (US); Vijay Nanda, Houston, TX (US); Maruti Bhandarkar, East Weymouth, MA (US); Joseph C. Peters, Quincy, MA (US); Chung-Ming Chi, Needham, MA (US); Brian Maerz, Chelmsford, MA (US)

(73) Assignees: ExxonMobil Chemical Patents Inc., Houston, TX (US); Stone & Webster, Inc., Baton Rouge, LA (US)

( * ) Notice: Subject to any disclaimer, the term of this patent is extended or adjusted under 35 U.S.C. 154(b) by 446 days.

(21) Appl. No.: 11/881,921

(22) Filed: Jul. 30, 2007

(65) Prior Publication Data

US 2009/0036722 A1 Feb. 5, 2009

(51) Int. Cl.
*C07C 2/66* (2006.01)

(52) U.S. Cl. .......... 585/449; 585/467
(58) Field of Classification Search .......... 585/449, 585/467
See application file for complete search history.

(56) References Cited

U.S. PATENT DOCUMENTS

| | | | |
|---|---|---|---|
| 3,751,504 A | 8/1973 | Keown et al. |
| 3,751,506 A | 8/1973 | Burress |
| 3,755,483 A | 8/1973 | Burress |
| 4,016,218 A | 4/1977 | Haag et al. |
| 4,891,458 A | 1/1990 | Innes et al. |
| 4,992,606 A | 2/1991 | Kushnerick et al. |
| 5,149,894 A | 9/1992 | Holtermann et al. |
| 5,258,565 A | 11/1993 | Kresge et al. |
| 5,371,310 A | 12/1994 | Bennett et al. |
| 5,453,554 A | 9/1995 | Cheng et al. |
| 5,476,978 A | 12/1995 | Smith et al. |
| 5,942,650 A | 8/1999 | Gajda |
| 6,077,498 A | 6/2000 | Diaz Cabanas et al. |
| 6,231,751 B1 | 5/2001 | Canos et al. |
| 6,252,126 B1 | 6/2001 | Netzer |
| 6,376,729 B1 | 4/2002 | Merrill et al. |
| 6,995,295 B2 | 2/2006 | Clark et al. |

FOREIGN PATENT DOCUMENTS

| | | |
|---|---|---|
| EP | 0432814 | 6/1991 |
| EP | 0629549 | 12/1994 |
| EP | 1188734 | 3/2002 |

*Primary Examiner*—Thuan Dinh Dang

(57) ABSTRACT

A process is described for producing an alkylaromatic compound, in which a first feed comprising an alkylatable aromatic compound and a second feed comprising an alkene are introduced into a first alkylation reaction zone comprising a first alkylation catalyst. The first alkylation reaction zone is operated under conditions effective to cause alkylation of the alkylatable aromatic compound by the alkene to produce said alkylaromatic compound, the conditions being such that the alkylatable aromatic compound is at least predominantly in the vapor phase. A first effluent comprising the alkylaromatic compound and unreacted alkylatable aromatic compound is withdrawn from the first alkylation reaction zone and at least part of the unreacted alkylatable aromatic compound is treated to remove catalyst poisons therefrom and produce a treated unreacted alkylatable aromatic stream. At least part of the unreacted alkylatable aromatic compound and a third feed comprising said alkene is introduced into a second alkylation reaction zone comprising a second alkylation catalyst. The second alkylation reaction zone is operated under conditions effective to cause alkylation of the unreacted alkylatable aromatic compound by the alkene to produce said alkylaromatic compound, the conditions being such that the alkylatable aromatic compound is at least predominantly in the liquid phase. A second effluent comprising said alkylaromatic compound is withdrawn from the second alkylation reaction zone.

21 Claims, 2 Drawing Sheets

ALKYLAROMATICS PRODUCTION

FIELD

The present invention relates to a process for producing alkylaromatic compounds, particularly ethylbenzene.

BACKGROUND

Ethylbenzene is a key raw material in the production of styrene and is produced by the reaction of ethylene and benzene in the presence of an acid catalyst. Old ethylbenzene production plants, typically built before 1980, used $AlCl_3$ or $BF_3$ as the acidic catalyst. Newer plants have in general been switching to zeolite-based acidic catalysts.

Traditionally, ethylbenzene has been produced in vapor-phase reactor systems, in which the ethylation reaction of benzene with ethylene is carried out at a temperature of about 380-420° C. and a pressure of 9-15 kg/cm$^2$-g in multiple fixed beds of zeolite catalyst. Ethylene exothermally reacts with benzene to form ethylbenzene, although undesirable chain and side reactions also occur. About 15% of the ethylbenzene formed further reacts with ethylene to form di-ethylbenzene isomers (DEB), tri-ethylbenzene isomers (TEB) and heavier aromatic products. All these chain reaction products are commonly referred as polyethylated benzenes (PEBs). In addition to the ethylation reactions, the formation of xylene isomers as trace products occurs by side reactions. This xylene formation in vapor phase processes may yield an ethylbenzene product with about 0.05-0.20 wt. % of xylenes. The xylenes show up as an impurity in the subsequent styrene product, and are generally considered undesirable.

In order to minimize the formation of PEBs, a stoichiometric excess of benzene, about 400-2000% per pass, is applied, depending on process optimization. The effluent from the ethylation reactor contains about 70-85 wt. % of unreacted benzene, about 12-20 wt. % of ethylbenzene product and about 3-4 wt. % of PEBs. To avoid a yield loss, the PEBs are converted back to ethylbenzene by transalkylation with additional benzene, normally in a separate transalkylation reactor.

By way of example, vapor phase ethylation of benzene over the crystalline aluminosilicate zeolite ZSM-5 is disclosed in U.S. Pat. No. 3,751,504 (Keown et al.), U.S. Pat. No. 3,751,506 (Burress), and U.S. Pat. No. 3,755,483 (Burress).

In recent years the trend in industry has been to shift away from vapor phase reactors to liquid phase reactors. Liquid phase reactors operate at a temperature of about 180-270° C., which is under the critical temperature of benzene (about 290° C.). One advantage of the liquid phase reactor is the very low formation of xylenes and other undesirable byproducts. The rate of the ethylation reaction is normally lower compared with the vapor phase, but the lower design temperature of the liquid phase reaction usually economically compensates for the negatives associated with the higher catalyst volume. Thus, due to the kinetics of the lower ethylation temperatures, resulting from the liquid phase catalyst, the rate of the chain reactions forming PEBs is considerably lower; namely, about 5-8% of the ethylbenzene is converted to PEBs in liquid phase reactions versus the 15-20% converted in vapor phase reactions. Hence the stoichiometric excess of benzene in liquid phase systems is typically 150-400%, compared with 400-2000% in vapor phase.

Liquid phase ethylation of benzene using zeolite beta as the catalyst is disclosed in U.S. Pat. No. 4,891,458 and European Patent Publication Nos. 0432814 and 0629549. More recently it has been disclosed that MCM-22 and its structural analogues have utility in these alkylation/transalkylation reactions, see, for example, U.S. Pat. No. 4,992,606 (MCM-22), U.S. Pat. No. 5,258,565 (MCM-36), U.S. Pat. No. 5,371,310 (MCM-49), U.S. Pat. No. 5,453,554 (MCM-56), U.S. Pat. No. 5,149,894 (SSZ-25); U.S. Pat. No. 6,077,498 (ITQ-1); and U.S. Pat. No. 6,231,751 (ITQ-2).

Although liquid phase ethylbenzene plants offer significant advantages over vapor phase processes, because they necessarily operate at lower temperatures, liquid phase processes tend to be more sensitive to catalyst poisons than their vapor phase counterparts, making them of limited utility with lower grade ethylene and benzene streams without significant feed pretreatment. However, the purification of alkylation feed streams is a costly business and hence there is considerable interest in developing processes that may operate with lower grade feed streams.

The present invention provides an aromatics alkylation process that allows the use of a dilute alkene feed, in which the aromatics feedstock is initially subjected to a vapor phase alkylation stage and then at least part of the unreacted aromatics feedstock is subjected to a liquid phase alkylation stage. In this way, the advantages of vapor phase alkylation, particularly decreased susceptibility to catalyst poisons, can be combined with the advantages of liquid phase alkylation, decreased capital cost and lower level of by-products. At least part of the effluent from the vapor phase alkylation stage undergoes interstage treatment to remove catalyst poisons before passing to the liquid phase alkylation stage.

U.S. Pat. No. 6,376,729 discloses a process for the production of ethylbenzene by the gas phase alkylation of benzene over a molecular sieve aromatic alkylation catalyst followed by liquid phase alkylation of the product of the gas phase alkylation. A feedstock containing benzene and ethylene is supplied to a first alkylation reaction zone containing a molecular sieve aromatic alkylation catalyst. The reaction zone is operated at temperature and pressure conditions to cause gas phase ethylation of the benzene with the production of an alkylation product comprising a mixture of ethylbenzene and a polyalkylated aromatic component including diethylbenzene. At least part of the output from the first alkylation reaction zone is supplied, without pretreatment, to a second alkylation zone which is operated in the liquid phase or in the supercritical region followed by supply to an intermediate recovery zone for the separation and recovery of ethylbenzene and a polyalkylated aromatic compound component including diethylbenzene.

European Patent No. 1,188,734 B1 discloses a process for the production of ethylbenzene similar to that disclosed in U.S. Pat. No. 6,376,729, except at least part of the polyalkylated aromatic component from the first gas phase alkylation reaction zone is reacted with additional benzene in a transalkylation zone and the effluent from the transalkylation zone is supplied to the second liquid phase alkylation zone.

SUMMARY

In one aspect, the present invention resides in a process for producing an alkylaromatic compound, the process comprising:

(a) introducing a first feed comprising an alkylatable aromatic compound and a second feed comprising an alkene into a first alkylation reaction zone comprising a first alkylation catalyst;

(b) operating said first alkylation reaction zone under conditions effective to cause alkylation of said alkylatable aromatic compound by said alkene to produce said alkylaromatic compound, said conditions being such that said alkylatable aromatic compound is at least predominantly in the vapor phase;

(c) withdrawing from said first alkylation reaction zone a first effluent comprising at least a portion of said alkylaromatic compound and unreacted alkylatable aromatic compound;

(d) treating at least part of said unreacted alkylatable aromatic compound to remove catalyst poisons therefrom and produce a treated unreacted alkylatable aromatic stream;

(e) introducing at least part of said treated unreacted alkylatable aromatic stream and a third feed comprising said alkene into a second alkylation reaction zone comprising a second alkylation catalyst;

(f) operating said second alkylation reaction zone under conditions effective to cause alkylation of at least a portion of said unreacted alkylatable aromatic compound by said alkene to produce said alkylaromatic compound, said conditions being such that said alkylatable aromatic compound is at least predominantly in the liquid phase; and (g) withdrawing from said second alkylation reaction zone a second effluent comprising said alkylaromatic compound.

In one embodiment, the pretreating step (d) is carried out in a pretreater. Conveniently, the pretreater contains a material, such as clay, activated carbon, alumina and/or a molecular sieve capable of removing nitrogen-containing impurities from said unreacted alkylatable aromatic compound.

Conveniently, the process further comprises (h) recycling at least part of said unreacted alkylatable aromatic compound from said first effluent to said first alkylation reaction zone.

Conveniently, said first feed comprises less than 80 wt. %, such as less than 65 wt. %, of said alkene and typically also comprises at least one alkane.

In one embodiment, said first alkylation catalyst comprises a molecular sieve selected from zeolite beta, a molecular sieve having a Constraint Index of 2-12, and a molecular sieve of the MCM-22 family. Conveniently, said second alkylation catalyst comprises zeolite beta and/or a molecular sieve of the MCM-22 family Conveniently, said first effluent also comprises polyalkylated aromatic compounds and the process further comprises:

(i) separating at least part of said polyalkylated aromatic compounds from said first effluent;

(j) introducing at least a portion of said separated polyalkylated aromatic compounds and a fourth feed comprising an alkylatable aromatic compound into a transalkylation reaction zone comprising a transalkylation catalyst;

(k) operating said transalkylation reaction zone under conditions effective to cause transalkylation of at least a portion of said separated polyalkylated aromatic compounds by said alkylatable aromatic compound to produce said alkylaromatic compound.

Conveniently, said second effluent also comprises polyalkylated aromatic compounds and the process further comprises:

(l) separating at least part of said polyalkylated aromatic compounds from said second effluent;

(m) introducing at least a portion of said polyalkylated aromatic compounds separated in (l) into said transalkylation reaction zone.

Conveniently, the conditions in said first alkylation reaction zone include a first temperature and the conditions in said second alkylation reaction zone include a second temperature lower than said first temperature.

In one embodiment, said alkene includes ethylene, said alkylatable aromatic compound includes benzene and said alkylaromatic compound includes ethylbenzene. Conveniently, said conditions in (b) include a temperature of about 350° C. to about 400° C. and a pressure of about 2000 kpa-a (kilopascal absolute) to about 3500 kPa-a. Conveniently, said conditions in (f) include a temperature of about 120° C. to about 270° C. and a pressure of about 675 kpa-a to about 8300 kPa-a.

DETAILED DESCRIPTION OF THE EMBODIMENTS

Figure 1:
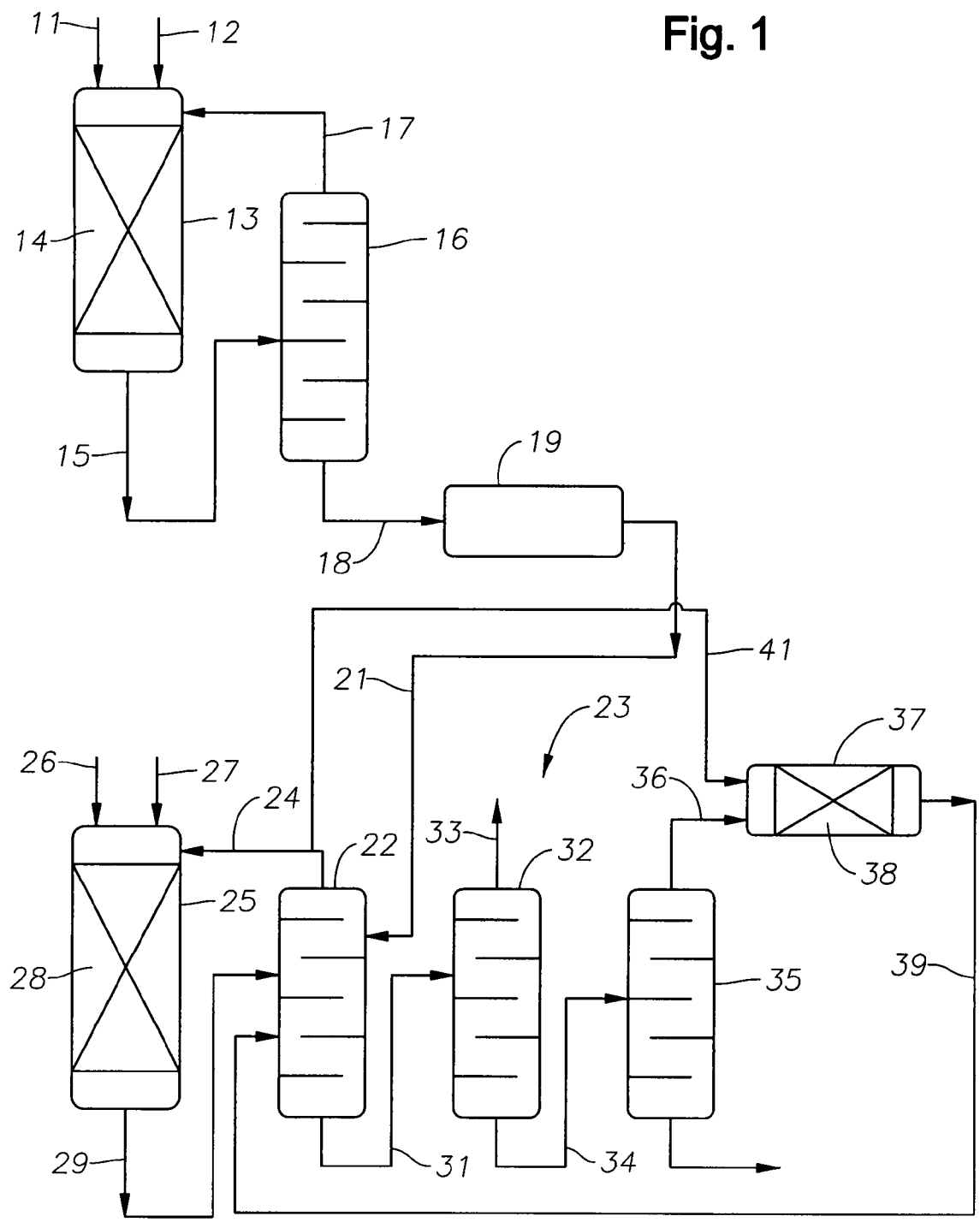
FIG. 1 is a flow diagram of a process for producing ethylbenzene in accordance with one embodiment of the invention.

The present invention provides a process for producing alkylaromatic compounds that combines vapor phase alkylation of an alkylatable aromatic compound with an alkene with liquid phase alkylation of unreacted aromatic compound from the vapor phase alkylation step. The vapor phase alkylation step is generally conducted at a relatively high first temperature whereas the liquid phase alkylation step is generally conducted at a lower second temperature. By operating at a relatively high temperature, the vapor phase alkylation step can be employed with less expensive feedstocks, including feedstocks containing significant levels of impurities, even sulfur and nitrogen-based impurities. Depending on the nature of the impurities present, the liquid phase alkylation step may be operated with the same dilute alkene feedstock as the vapor phase alkylation step or the feedstock may require initial pretreatment to remove deleterious impurities, such as nitrogen-based compounds.

Combining liquid phase alkylation with vapor phase alkylation also allows savings in capital investment by allowing older vapor phase units to be retained when newer liquid phase alkylation units are being installed.

The term "predominantly" in vapor phase or liquid phase, as used herein, means that more than 50 wt. %, preferably more than 75 wt. %, more preferably more than 90 wt. %, of the material is in vapor phase or liquid phase.

Although the present process is particularly directed to the production of ethylbenzene, it is equally applicable to the production of other $C_2$-$C_6$ alkylaromatic compounds, such as cumene and sec-butylbenzene, as well as $C_6$+ alkylaromatics, such as $C_8$-$C_{16}$ linear alkylbenzenes.

Reactants

The reactants used in the present process include an alkylatable aromatic compound and an alkene alkylating agent.

The term "aromatic" in reference to the alkylatable compounds which are useful herein is to be understood in accordance with its art-recognized scope which includes alkyl substituted and unsubstituted mono- and polynuclear compounds. Compounds of an aromatic character which possess a heteroatom are also useful provided they do not act as catalyst poisons under the reaction conditions selected.

Substituted aromatic compounds which may be alkylated herein must possess at least one hydrogen atom directly bonded to the aromatic nucleus. The aromatic rings may be substituted with one or more alkyl, aryl, alkaryl, alkoxy, aryloxy, cycloalkyl, halide, and/or other groups which do not interfere with the alkylation reaction.

Suitable aromatic hydrocarbons include benzene, naphthalene, anthracene, naphthacene, perylene, coronene, and phenanthrene, with benzene being preferred.

Generally the alkyl groups which may be present as substituents on the aromatic compound contain from about 1 to 22 carbon atoms and usually from about 1 to 8 carbon atoms, and most usually from about 1 to 4 carbon atoms.

Suitable alkyl substituted aromatic compounds include toluene, xylene, isopropylbenzene, normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons may also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$.

Reformate or a cut thereof containing substantial quantities of benzene, toluene and/or xylene constitutes a particularly useful feed for the alkylation process of this invention.

The alkylating agent useful in the present process includes an alkene, which can be present as substantially pure alkene feed or as a dilute feed containing at least one alkane and typically at least one alkane having the same number of carbon atoms as the alkene. For example, where the alkene is ethylene, the alkane may be ethane. Typically, the dilute alkene feed comprises at least 20 wt. % of the alkene, such as from about 20 to about 80 wt. %, for example from about 60 to about 80 wt. %, of the alkene. It is recognized that feed sources may undergo purification (for example by distillation) prior to being fed to the present process. One particularly useful feed is the dilute ethylene stream obtained as an off gas from the fluid catalytic cracking unit of a petroleum refinery.

Preferably, the reactants in the present process are benzene and ethylene and the desired reaction product is ethylbenzene.

Vapor Phase Alkylation

The first step in the present process involves reacting the alkylatable aromatic compound with the alkene feedstock in a first alkylation reaction system comprising one or a plurality of series-connected alkylation reaction zones, which each contain an alkylation catalyst and which are typically located in a single reaction vessel. The or each alkylation reaction zone in the first alkylation reaction system is operated under conditions effective to ensure that said alkylatable aromatic compound is at least predominantly in the vapor phase. Typically, where the alkylatable aromatic compound includes benzene, the alkene includes ethylene and the alkylaromatic compound includes ethylbenzene, the conditions in the or each alkylation reaction zone of the first alkylation reaction system include a temperature of about 350° C. to about 400° C. and a pressure of about 2000 kPa-a to about 3500 kpa-a.

In one embodiment, the alkylation catalyst employed in the or each alkylation reaction zone of the vapor phase alkylation reaction system comprises at least one medium pore molecular sieve having a Constraint Index of 2-12 (as defined in U.S. Pat. No. 4,016,218). Suitable medium pore molecular sieves include ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231.

In another embodiment, the alkylation catalyst employed in the or each alkylation reaction zone of the vapor phase alkylation reaction system comprises at least one molecular sieve of the MCM-22 family. As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof.

In a further embodiment, the alkylation catalyst employed in the or each alkylation reaction zone of the vapor phase alkylation reaction system comprises one or more large pore molecular sieves having a Constraint Index less than 2. Suitable large pore molecular sieves include zeolite beta, zeolite Y, Ultrastable Y (USY), Dealuminized Y (Deal Y), mordenite, ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Zeolite Beta is described in U.S. Pat. No. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

Preferred molecular sieves for the vapor phase alkylation reaction comprise zeolite beta, molecular sieves having a Constraint Index of 2-12, especially ZSM-5, and molecular sieves of the MCM-22 family.

The above molecular sieves may be used as the vapor phase alkylation catalyst without any binder or matrix, i.e., in so-called self-bound form. Alternatively, the molecular sieve may be composited with another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 percent by weight and more usually, particularly, when the composite is prepared in the form of beads, in the range of about 2 to about 80 weight percent of the composite.

Treatment of the Vapor Phase Alkylation Effluent

The effluent from the vapor phase alkylation reaction system comprises the desired alkylaromatic compound, together with polyalkylated species, such as di- and triethylbenzene, unreacted alkylatable aromatic compound, any unreacted alkene (overall alkene conversion is expected to be 98-99.99+%) and any unreactive impurities present in the original alkene and aromatic feeds. Examples of typical impurities include N-methylpyrrolidone (NMP) and sulfolane typically present in benzene feedstocks and dimethylformamide (DMF) often present in ethylene feeds. Depending on the nature of these unreactive impurities, they could adversely affect the downstream liquid phase alkylation step and hence part or all of the vapor phase alkylation effluent treated before being fed to liquid phase alkylation system. In one embodiment, the treating step is carried out in a pretreater. The pretreater is designed to remove catalyst poisons from the vapor phase alkylation effluent and typically contains a material, such as clay, activated carbon, alumina and/or a molecular sieve, capable of removing sulfur and nitrogen-containing impurities from the effluent. The pretreater is typically operated at a temperature of about 25° C. to about 200° C.

After passage through the pretreater, the vapor phase alkylation effluent is fed to a product separation system where the unreacted alkylatable aromatic compound is separated from the desired alkylaromatic compound and any polyalkylated species before being fed to the liquid phase alkylation system. In some cases, prior to feeding the vapor phase alkylation effluent to the pretreater, it may be desirable to subject the effluent to an initial fractionation step to remove part of the unreacted alkylatable aromatic compound for recycle to the vapor phase alkylation system and, if necessary to remove water that may have been present in the fresh benzene feed.

Liquid Phase Alkylation

After removal of catalyst poisons in the pretreater, at least part of the unreacted alkylatable aromatic compound in the vapor phase alkylation effluent is reacted with additional alkene feedstock in a second liquid phase alkylation reaction system. The second alkylation system comprises one or a plurality of series-connected alkylation reaction zones, each containing an alkylation catalyst and each typically located in a single reaction vessel. The or each alkylation reaction zone in the second alkylation reaction system is operated under conditions effective to cause alkylation of the unreacted alkylatable aromatic compound by the additional alkene to produce said alkylaromatic compound, while ensuring that the alkylatable aromatic compound is at least predominantly in the liquid phase. Typically, this means that the temperature employed in each liquid phase alkylation reaction zone is less than the temperature employed in each vapor phase alkylation reaction zone. Thus, where the alkylatable aromatic compound includes benzene, the alkene includes ethylene and the alkylaromatic compound includes ethylbenzene, the conditions in the or each liquid phase alkylation reaction zone include a temperature of about 120° C. to about 270° C. and a pressure of about 675 kPa-a to about 8300 kPa-a.

The alkene feedstock employed in the second liquid phase alkylation reaction system can be the same as or different from the alkene feedstock employed in the first vapor phase alkylation reaction system, although the alkene component in each feedstock will generally be the same, such as ethylene. In particular, if the vapor phase alkene feedstock contains nitrogenous impurities, a different feedstock or the same feedstock but treated to remove the nitrogenous impurities will generally be used for the liquid phase reaction. Typically, the vapor phase alkene feedstock can contain up to 0.01 wt. % nitrogen-containing impurities as elemental nitrogen, whereas the liquid phase alkene feedstock should contain less than 0.001 wt. % nitrogen-containing impurities as elemental nitrogen.

For example, treatment of the liquid phase alkene feedstock to remove nitrogenous impurities can be achieved by providing a by-passable reactive guard bed upstream of the second liquid phase alkylation reaction system. The reactive guard bed is also loaded with alkylation catalyst, which may be the same of different from the catalyst used in the or each liquid phase alkylation reaction zone, and is maintained under ambient or up to alkylation conditions. The alkylatable aromatic compound and at least a portion of the alkene feedstock are passed through the reactive guard bed prior to entry into the or the first liquid phase alkylation reaction zone. The reactive guard bed not only serves to effect the desired alkylation reaction but is also used to remove any reactive impurities in the feeds, such as nitrogen compounds, which could otherwise poison the remainder of the liquid phase alkylation catalyst. The catalyst in the guard bed is therefore subject to more frequent regeneration and/or replacement than the remainder of the liquid phase alkylation catalyst and hence the guard bed is normally provided with a by-pass circuit so that the alkylation feedstocks may be fed directly to the liquid phase alkylation reaction system when the guard bed is out of service.

The alkylation catalyst employed in the or each alkylation reaction zone of the liquid phase alkylation reaction system can comprise one or more of any of the molecular sieves discussed above in relation to the vapor phase alkylation system and can be used with or without a binder or matrix. Generally, however, the liquid phase alkylation catalyst is selected from zeolite beta and a molecular sieve of the MCM-22 family.

In addition to the desired alkylaromatic product, the effluent from the liquid phase alkylation step tends to contain significant quantities of unreacted alkylatable aromatic compound and, in some cases, it may be desirable to remove at least part of said unreacted alkylatable aromatic compound and recycle it to the liquid phase alkylation step.

Transalkylation

The effluent from the vapor phase alkylation system, and to a lesser extent the effluent from the liquid phase alkylation system, will tend to contain polyalkylated aromatic compounds. Thus both effluents are passed to the product separation system that not only serves to remove unreacted alkylated aromatic compound, and desired monoalkylated product, but also separates the polyalkylated species. The polyalkylated species are then fed to a transalkylation reactor, which is normally separate from the alkylation reactor, where additional monoalkylated product is produced by reacting the polyalkylated species with additional aromatic compound in the presence of a transalkylation catalyst. Typically, the transalkylation reactor is operated under conditions such that the polyalkylated aromatic compounds and the alkylatable aromatic compound are at least predominantly in the liquid phase.

For example, suitable conditions for carrying out the liquid phase transalkylation of benzene with polyethylbenzenes may include a temperature of from about 150° C. to about 260° C., a pressure of 7000 kPa-a or less, a WHSV based on the weight of the total liquid feed to the reaction zone of from about 0.5 to about 100 hr$^{-1}$ and a mole ratio of benzene to polyethylbenzene of from about 1:1 to about 30:1. Particular conditions for carrying out the liquid phase transalkylation of benzene with polypropylbenzenes may include a temperature of from about 150° C. to about 300° C., a pressure of 5500 kPa-a or less, a WHSV based on the weight of the total liquid feed to the reaction zone of from about 0.1 to about 20.0 hr$^{-1}$ and a mole ratio of benzene to polypropylbenzene of from about 1.0 to about 10.0. Particular conditions for carrying out the liquid phase transalkylation of benzene with polybutylbenzenes may include a temperature of 100 to 300° C., a pressure of 1000 to 7000 kpa-a, a weight hourly space velocity of 1 to 50 hr$^{-1}$ on total feed, and a benzene to polybutylbenzene weight ratio of 1 to 10.

The transalkylation catalyst can comprise one or more of any of the molecular sieves discussed above in relation to the vapor phase alkylation system and can be used with or without a binder or matrix. Generally, however, the transalkylation catalyst is selected from zeolite beta, zeolite Y, Ultrastable Y (USY), Dealuminized Y (Deal Y), mordenite, ZSM-3, ZSM-4, ZSM-5, ZSM-11, ZSM-18, and ZSM-20.

One embodiment of the present process, in which the alkylatable aromatic compound is benzene and the alkylating agent is a dilute ethylene stream, is shown in FIG. 1.

Referring to FIG. 1, benzene and the dilute ethylene feed are supplied through lines 11, 12 respectively to a first alkylation reactor 13. The reactor 13 contains a first alkylation catalyst 14, such as ZSM-5, and is operated under conditions such that the benzene is predominantly in the vapor phase and reacts with the ethylene to produce a first alkylation effluent containing ethylbenzene, polyethylated benzenes and unreacted benzene.

The first alkylation effluent exits the reactor 13 through line 15 and is fed to a prefractionator 16 where part, but not all, of the unreacted benzene is separated from the effluent as overhead 17 and is recycled to the reactor 13. The remainder of the first alkylation effluent exits the prefractionator 16 through line 18 and is fed to a pretreater 19 containing clay, alumina and/or a molecular sieve. The pretreater removes nitrogen-containing impurities from the first alkylation effluent, which is then fed by line 21 to a benzene column 22 of a product separation system 23.

The benzene column 22 removes additional unreacted benzene from the first alkylation effluent and supplies the unreacted benzene through line 24 to a second alkylation reactor 25, which receives make-up benzene through line 26 and additional ethylene through line 27. A part of the benzene recovered from the benzene column 22 is fed via line 41 to a transalkylation reactor 37. The reactor 25 contains a second alkylation catalyst 28, such as MCM-22, and is operated under conditions such that the benzene is predominantly in the liquid phase and reacts with the ethylene to produce a second alkylation effluent containing ethylbenzene, polyethylated benzenes and unreacted benzene.

The second alkylation effluent exits the reactor 25 through line 29 and is fed to the benzene column 22, where the first and second alkylation effluents are combined. After removal of the unreacted benzene through line 24, the remainder of the first and second alkylation effluents is fed by line 31 to an ethylbenzene column 32, where the desired ethylbenzene product is recovered as overhead 33. The bottoms 34 from the ethylbenzene column 32 is then fed to a polyethylbenzene column 35, where the polyethylated benzenes are removed through line 36 and supplied to a transalkylation reactor 37.

The reactor 37 contains a transalkylation catalyst 38, such as zeolite Y, and is operated under conditions such that the polyethylated benzenes and benzene are predominantly in the liquid phase and react to produce a transalkylation effluent containing ethylbenzene and unreacted polyethylated benzenes and unreacted benzene. The transalkylation effluent exits the reactor 37 through line 39 and is recycled to the benzene column 22.

The invention will now be more particularly described with reference to the following Example.

EXAMPLE 1

Benzene and ethylene were fed to a 4-stage fixed-bed commercial reactor operated in a downflow configuration. The catalyst was a ZSM-5 extrudate containing more than 40% zeolite. The operating conditions in the reactor were an inlet temperature of 390° C. and a pressure of 2370 kpa-a so that the benzene was in the vapor phase. The molar ratio of benzene to ethylene in the first reactor was 6.4 and the weight hour space velocity on olefin fed is less than 50.0 hr$^{-1}$ to achieve greater than 99.7% olefin conversion.

The effluent from the vapor phase alkylation reactor contained ethylbenzene (EB) and unreacted benzene and was fed to a pretreater containing at least one adsorbent selected from Engelhard F-24 clay, zeolite 13X, and Selexsorb CD alumina and maintained at a temperature of approximately 30° C. The treated effluent was then fed to a benzene distillation column where the unreacted benzene was separated from the effluent and fed, with additional ethylene, to a 6 stage fixed-bed micro-reactor containing a total of 96 g of catalyst being operated in a downflow configuration. The catalyst was an MCM-22 extrudate containing more than 40% zeolite. The operating conditions in the second reactor included a molar ratio of benzene to ethylene of 2.8, a temperature of 185° C. and a pressure of 3600 kPa-a so that the benzene was in the liquid phase. The WHSV on olefin was approximately 1.0 $hr^{-1}$ to achieve greater than 99.7% olefin conversion. A ¾" pipe was used for the reaction vessel and the catalyst bed interstitial spaces were filled with inert sand to avoid reactant bypassing. The total product was chilled and analyzed with an off-line gas chromatograph equipped with a flame ionization detector.

The internal temperature in the catalyst bed of the second reactor was measured using a multipoint thermocouple probe inserted axially in the bed. The results are shown in FIG. 2 which plots time on stream versus the percent temperature rise (ΔT %) at a given axial location in the catalyst bed of the second reactor, where:

ΔT%=(temperature at a given point in the catalyst bed–the inlet temperature)/(total temperature rise across the entire catalyst bed)

Figure 2:
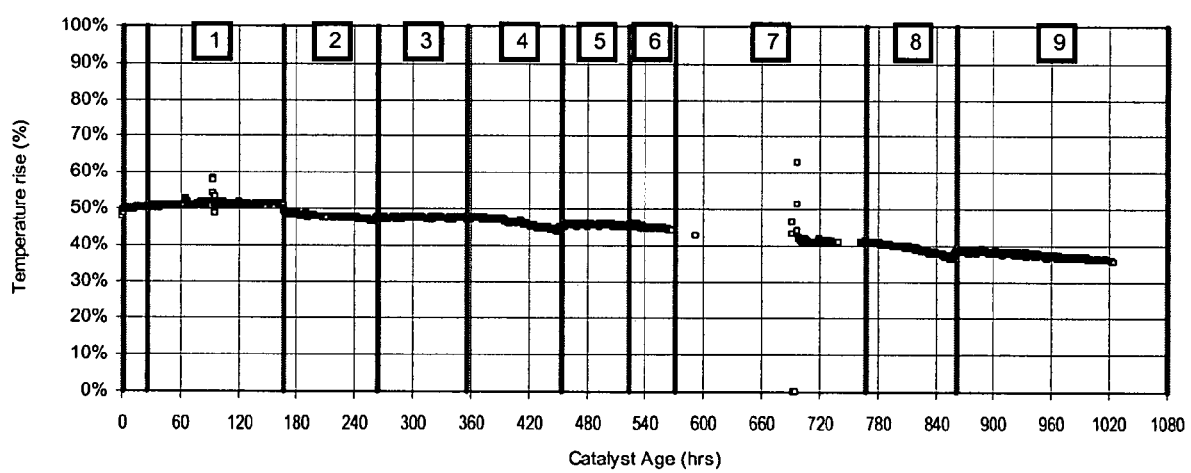
FIG. 2 is a graph plotting temperature rise against time on stream at different points in the catalyst bed employed of the second fixed-bed micro-reactor of Example 1.

Referring to FIG. 2, the first time period labeled "1" represents an operating condition in which crude EB-containing effluent from the vapor phase first alkylation reactor was passed through a pretreatment bed of Engelhard F-24 clay before the unreacted benzene was separated and fed to the second reactor. The temperature profiles in this condition are flat representing stable catalyst activity.

The second time period labeled "2" in FIG. 2 indicates a condition in which the same feed from the first time period was used, but the clay pretreaters were by-passed such that the crude EB-containing effluent from the vapor phase first alkylation reactor did not receive any pretreatment. After by passing the guard beds, an immediate step-change is observed followed by a decrease in the 36.6% temperature profile from around 49% to around 47%. This decline in temperature profile represents catalyst deactivation which occurs when the crude EB-containing effluent is not pretreated.

The third time period labeled "3" represents the same operating condition as the first time period—that is the clay pretreatment guard bed was brought back online. As shown, the temperature profile during this period is flat, representing stable catalyst activity without deactivation with clay pretreatment of the crude EB-containing effluent.

The fourth time period labeled "4" represents the same operating condition as the second time period, that is without clay pretreatment the crude EB-containing effluent from the vapor phase first alkylation reactor. In this time period as in second time period, catalyst deactivation occurs with the temperature profile dropping from ~47% to ~43% at the 36.6% position in the bed.

The fifth time period labeled "5" represents the operating condition in which EB-containing effluent from the vapor phase first alkylation reactor is pretreated with both clay and 13X molecular sieve. Again stable activity is observed.

The sixth time period labeled "6" represents the operating condition in which EB-containing effluent from two different drums (#3 and #2) was used and was pretreated with zeolite 13X alone. As in the case where clay was used alone, 13X pretreatment was also able to maintain stable catalyst activity.

The seventh time period labeled "7" represents an operating condition in which benzene supplied Spectrum Chemicals & Laboratory Products was fed to the second reactor in place of the unreacted benzene from the first reactor effluent. This benzene was not pretreated. No deactivation was observed with this benzene even without pretreatment.

The eighth time period labeled "8" represents an operating condition where crude EB-containing effluent from the vapor phase first alkylation reactor was reintroduced into the unit in place of the Spectrum benzene. No clay was used and the guard beds were bypassed. In this case deactivation from ~41% to ~37% was observed.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A process for producing an alkylaromatic compound, the process comprising:
   (a) introducing a first feed comprising an alkylatable aromatic compound and a second feed comprising an alkene into a first alkylation reaction zone comprising a first alkylation catalyst comprising a molecular sieve selected from the group consisting of zeolite beta, a molecular sieve having a Constraint Index of 2-12, and a molecular sieve of the MCM-22 family;
   (b) operating said first alkylation reaction zone under conditions effective to cause alkylation of said alkylatable aromatic compound by said alkene to produce said alkylaromatic compound, said conditions being such that said alkylatable aromatic compound is in the vapor phase;
   (c) withdrawing from said first alkylation reaction zone a first effluent comprising at least a portion of said alkylaromatic compound and unreacted alkylatable aromatic compound;
   (d) treating at least part of said unreacted alkylatable aromatic compound to remove catalyst poisons by contacting said unreacted alkylatable aromatic compound with a material capable of removing sulfur-containing and/or nitrogen-containing impurities from said unreacted alkylatable aromatic compound therefrom and produce a treated unreacted alkylatable aromatic stream;
   (e) introducing at least part of said treated unreacted alkylatable aromatic stream and a third feed comprising said alkene into a second alkylation reaction zone comprising a second alkylation catalyst comprising zeolite beta and/or a molecular sieve of the MCM-22 family;
   (f) operating said second alkylation reaction zone under conditions effective to cause alkylation of at least a portion of said unreacted alkylatable aromatic compound by said alkene to produce said alkylaromatic compound, said conditions being such that said alkylatable aromatic compound is in the liquid phase; and
   (g) withdrawing from said second alkylation reaction zone a second effluent comprising said alkylaromatic compound.

2. The process of claim 1, wherein said treating step comprises contacting said unreacted alkylatable aromatic compound with clay, activated carbon, alumina and/or a molecular sieve.

3. The process of claim 1 and further comprising:
   (h) recycling at least part of said unreacted alkylatable aromatic compound from said first effluent to said first alkylation reaction zone.

4. The process of claim 1, wherein said first effluent also comprises polyalkylated aromatic compounds and the process further comprises:

(i) separating at least part of said polyalkylated aromatic compounds from said first effluent;

(j) introducing at least a portion of said separated polyalkylated aromatic compounds and a fourth feed comprising an alkylatable aromatic compound into a transalkylation reaction zone comprising a transalkylation catalyst;

(k) operating said transalkylation reaction zone under conditions effective to cause transalkylation of said separated polyalkylated aromatic compounds by said alkylatable aromatic compound to produce said alkylaromatic compound.

5. The process of claim 1, wherein said second effluent also comprises unreacted alkylatable aromatic compound and the process further comprises:

(l) recycling at least part of said unreacted alkylatable aromatic compound from said second effluent to said second alkylation reaction zone.

6. The process of claim 1, wherein said second effluent also comprises polyalkylated aromatic compounds and the process further comprises:

(m) separating at least part of said polyalkylated aromatic compounds from said second effluent;

(n) introducing at least a portion of said polyalkylated aromatic compounds separated in (l) into said transalkylation reaction zone.

7. The process of claim 6, wherein said conditions in said transalkylation reaction zone are such that said polyalkylated aromatic compounds and said alkylatable aromatic compound are at least predominantly in the liquid phase.

8. The process of claim 6, wherein said transalkylation catalyst includes a molecular sieve selected from the group consisting of zeolite beta, zeolite Y, Ultrastable Y (USY), Dealuminized Y (DealY), mordenite, ZSM-3, ZSM-4, ZSM-5, ZSM-11, ZSM-18, and ZSM-20.

9. The process of claim 1, wherein said first alkylation catalyst comprises a molecular sieve of the MCM-22 family selected from the group consisting of MCM-22, PSH-3, SSZ-25, ERB-1, ITQ-1, ITQ-2, ITQ-30, MCM-36, MCM-49, MCM-56, UZM-8 and mixtures thereof.

10. The process of claim 1, wherein said second alkylation catalyst comprises a molecular sieve of the MCM-22 family selected from the group consisting of MCM-22, PSH-3, SSZ-25, ERB-1, ITQ-1, ITQ-2, ITQ-30, MCM-36, MCM-49, MCM-56, UZM-8 and mixtures thereof.

11. The process of claim 1, wherein said first feed comprises less than 80 wt. % of said alkene.

12. The process of claim 1, wherein said first feed comprises less than 65 wt. % of said alkene.

13. The process of claim 1, wherein said second feed comprises less than 0.001 wt. % of nitrogen-containing impurities measured as elemental nitrogen.

14. The process of claim 1, wherein the conditions in said first alkylation reaction zone include a first temperature and the conditions in said second alkylation reaction zone include a second temperature lower than said first temperature.

15. The process of claim 1, wherein said alkene includes ethylene, said alkylatable aromatic compound includes benzene and said alkylaromatic compound includes ethylbenzene.

16. The process of claim 15, wherein said conditions in (b) include a temperature of about 350° C. to about 400° C. and a pressure of about 2000 kpa-a to about 3500 kPa-a.

17. The process of claim 15, wherein said conditions in (f) include a temperature of about 120° C. to about 270° C. and a pressure of about 675 kpa-a to about 8300 kpa-a.

18. The process of claim 1, wherein said first alkylation catalyst is ZSM-5 and the second alkylation catalyst is MCM-22.

19. The process of claim 1, wherein said first alkylation catalyst is ZSM-5 and the second alkylation catalyst is MCM-49.

20. The process of claim 1, wherein said first alkylation catalyst is ZSM-5 and the second alkylation catalyst is MCM-56.

21. The process of claim 1, wherein said first alkylation catalyst is ZSM-5 and the second alkylation catalyst is UZM-8.

* * * * *